(12) United States Patent
Fenchel et al.

(10) Patent No.: US 8,150,122 B2
(45) Date of Patent: *Apr. 3, 2012

(54) METHOD FOR CONTROLLING AN IMAGE DATA ACQUISITION AND/OR EVALUATION PROCEDURE IN MEDICAL EXAMINATIONS

(75) Inventors: Matthias Fenchel, Erlangen (DE); Andreas Schilling, Gomaringen (DE); Stefan Thesen, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 560 days.

This patent is subject to a terminal disclaimer.

(21) Appl. No.: 12/366,765

(22) Filed: Feb. 6, 2009

(65) Prior Publication Data

US 2009/0202121 A1   Aug. 13, 2009

(30) Foreign Application Priority Data

Feb. 7, 2008   (DE) .......................... 10 2008 007 827

(51) Int. Cl.
*G06K 9/00*   (2006.01)
(52) U.S. Cl. ....................................... 382/128; 382/131
(58) Field of Classification Search .................. 382/131, 382/154, 285, 294, 299
See application file for complete search history.

(56) References Cited

U.S. PATENT DOCUMENTS 7,899,227 B2 *   3/2011   Fenchel et al. ................ 382/128
2007/0242865 A1   10/2007   Fenchel et al.

FOREIGN PATENT DOCUMENTS

DE   102006017932   * 10/2007

OTHER PUBLICATIONS

"A Unified Framework for Atlas Matching Using Active Appearance Models," Cootes et al, Information Processing in Medical Imaging, vol. 1613 (1999) pp. 322-333.
"Statistical Models of Appearance for Medical Image Analysis and Computer Vision," Cootes et al, Prac. SPIE, vol. 4322 (2001) pp. 236-248.

* cited by examiner

*Primary Examiner* — Thanh X Luu
(74) *Attorney, Agent, or Firm* — Schiff Hardin LLP

(57) ABSTRACT

In a method to control the acquisition and/or evaluation procedure of image data in medical examinations, in a previously acquired planning image data set entirely or partially covering a target volume, spatial information of the target volume is determined automatically using a statistical model of the target volume based on data about real anatomy. The acquisition and/or evaluation operation is controlled using the spatial information. A statistical model of at least one greyscale value distribution in the region of the surface of the target volume is used to calculate the location information.

23 Claims, 7 Drawing Sheets

FIG 10
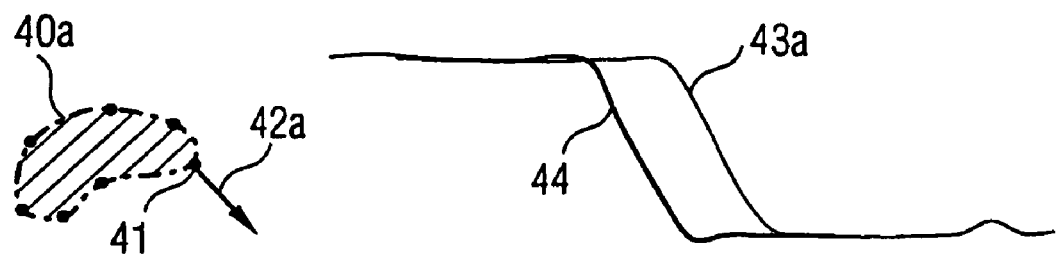
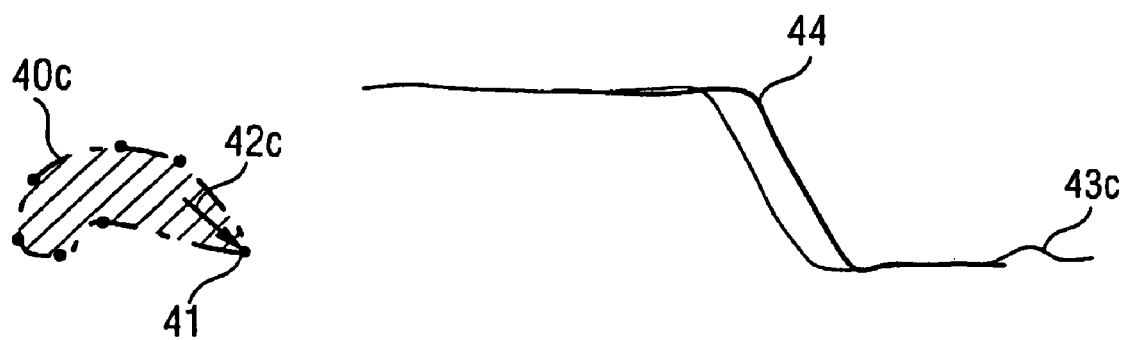

METHOD FOR CONTROLLING AN IMAGE DATA ACQUISITION AND/OR EVALUATION PROCEDURE IN MEDICAL EXAMINATIONS

BACKGROUND OF THE INVENTION

1. Field of the Invention

The present invention concerns a method to control the acquisition and/or evaluation procedure of image data in medical examinations of the type wherein, in a previously acquired planning image data set entirely or partially covering a target volume, location (spatial) information of the target volume is determined automatically using a statistical model of the target volume based on data about real anatomy, and the acquisition and/or evaluation procedure is controlled using the location information.

2. Description of the Prior Art

In serial examinations of pathologies or examinations of a possible medicinal effect on these pathologies, for the examiner it is extremely important to discover the precise orientation and positioning of the pathological object as quickly as possible. Since the resolution capability in small animal measurements is, for example, in the range of 100 µm and is in a range of half a millimeter in humans, prefabricated parameter sets cannot simply be adopted. Rather, the position and orientation of the subject to be examined must be rediscovered in every new examination. For this purpose, a planning image data set is typically acquired. The more precisely that the orientation of the subject to be examined should be determined, the greater the resolution of the planning image data set must be. If this panning image is three-dimensional, in magnetic resonance tomography acquisitions it is the case that, for doubled resolution in the phase coding directions, a measurement time that is twice as long must be scheduled. For a three-dimensional data set, two phase coding gradients are required, meaning that a doubled resolution in these two directions corresponds to a quadrupling of the measurement time. In addition, after this time-consuming acquisition, the positioning of the subject must still also be precisely determined by an operator in order to establish the parameter sets for subsequent acquisitions. An exact positioning of the measurement slice is therefore necessary since (for example in flow measurements) the measurement slice must be situated perpendicular to the vessel through which medium flows, because otherwise it artifacts can occur in the exposures. Such position determinations can thereby easily occupy half of the available measurement time. It is therefore desirable to be able to automatically and exactly register the position and orientation of the subject to be examined with an optimally low-resolution planning image data set.

DE 10 2006 017 932 A1 describes a method in which a target volume in a planning image data set is automatically determined using a statistical model of the target volume that is based on data about real anatomy, and the acquisition and/or evaluation operation is then controlled with this information. The statistical model is acquired by means of measurements on multiple test subjects.

SUMMARY OF THE INVENTION

An object of the invention is to provide a method of the above type that can be reproduced with less tendency toward error and that also requires less data for the planning image data set.

To solve this problem in a method of the aforementioned type, according to the invention a statistical model of at least one greyscale value distribution in the region of the surface of the target volume is used to calculate the spatial information.

In addition to the description of the target volume via a network of points, according to the invention the target volume is described by a network of profiles. Instead of one value, a series of values is thereby available for each point that should describe the target volume in a three-dimensional model. Spatial information thus can be obtained from the planning image data set entirely or partially covering the target volume in order to control the acquisition and/or evaluation operation of the target volume. The average model, thus the statistical model of the target volume that is based on data of real anatomy, is thereby adapted to the values of the planning image data set. The statistical average model is modified until the data of the planning image data set are reproduced with the highest probability.

A statistical model of the greyscale value distributions in the region of the surface of the target volume that is determined using model data sets of multiple people can be particularly advantageously used. Such a model has the advantage that it is based on real data, and that the statistical variance is reflected as close to reality as possible via suitable selection of people and, for example, MR method selection. It is also possible to divide the people into groups and thus to respectively achieve a model for children, women and men, for example, or to achieve a division based on age groups. The variance in the model data set can be reduced and the precision can thus be increased.

Correspondence points can advantageously be established on the surface of the target volume of each model data set. The volume of the data to be processed can be significantly reduced by this procedure. The more simply that the target volume is structured, the fewer correspondence points are required for description. For example, it is possible to register target volumes of relatively simple geometric structure (such as the liver or the kidneys) with relatively few correspondence points while more correspondence points are required for target volumes of more complex structure (such as the heart).

The greyscale values in the direction of the surface normals of each correspondence points of the target volume can advantageously be determined as profiles. The profiles are naturally dependent on their orientation relative to the surface. Optimally clear transitions from a target volume into regions outside the target value can be achieved by the selection of a preferred direction in the direction of the surface normals. A portion of the data points of the profile thereby lies within the target subject; some few lie in the transition regions, and multiple points additionally lie outside of the target subject. In the ideal case, the transition would ensue in stages, meaning that the transition from the target volume into the surrounding tissue would be recognizable as a jump in the greyscale values of the profile. In reality, however, for the most part one to two measurement points lie in this jump region, i.e. between the values that the target volume exhibits and the values that the surrounding tissue has. Conveniently, no exact point at which the surface of the target volume ends must be established via the use of the profile. Such an establishment is inherently always plagued with errors and can be omitted with the method according to the invention. After normalization of the profiles from the profiles of corresponding correspondence points for each correspondence point, an average profile representing the statistical model and a covariance matrix representing the statistical deviation can advantageously be determined. Statistical conclusions are possible only after measurement of at least one test subject; as already mentioned, these can also be divided into groups. In order to now obtain a statistical model from all of these target volumes of the model data sets, these must first be normalized, meaning that the value range of the variables must be transformed to a specific range. It is subsequently possible to determine an average profile and a covariance matrix for each correspondence point from the model data sets. This can also occur given group divisions, wherein only the model data sets associated with the group are then respectively incorporated into the generation of the average profile and the covariance matrix.

Alternatively, a reference image can be determined form the correspondence points of the model data sets via transformation of all test subject images to the average model. In this case, not only can the profiles be considered with regard to the surface normals of the correspondence points (thus this calculation of the reference image is computationally intensive); the statistical model outside of the measurements is created with test subjects, and this time factor is thus of less concern. The advantage lies in the fact that more data are available via the reference image. A normalized average image representing an additional statistical model and a normalized variance image representing the statistical deviation can then advantageously be determined from the reference image. By this procedure not only are profiles obtained with regard to the surface normals of the target volume, but also profiles of the greyscale value distribution in every direction relative to the surface of the target volume. A broader initial database is thus obtained.

Depending on the application field, various two-dimensional or three-dimensional data sets, or data sets from multiple two-dimensional images are considered as a planning image data set. It is possible for localizer exposures to be used as a planning image data set. The data acquired in such a manner are naturally subjected to one or more post-processing routines. For example, MR data are typically acquired in k-space and only converted into three-dimensional space via a Fourier transformation. In this post-processing the spatial resolution can then also be altered, for example by zero filling. Such reconstruction steps are necessary since the statistical model was naturally created in three-dimensional space from image data sets that have likewise previously been reconstructed. Since a statistical model based on real data is used (thus from the outset assumptions about the actual appearance of the target volume are plugged into the method), even low-resolution image data sets with a small coverage of the target area containing the target volume are sufficient, such that they can be used as a planning image data set. The term "coverage" is used herein to mean that, in the case of two-dimensional images, only thin sections are taken from the target volume, and thus a small slice thickness is realized. However, the spatial resolution of the actual image could be high. A smaller coverage is thus achieved with a small slice thickness and a low number of images. The method according to the invention here has a particularly advantageous field of application since these localizer exposures can already be produced before the additional data set acquisition.

Naturally it is also possible to use a previous diagnostic image data set as a planning image data set. Such a diagnostic image data set can have already been acquired for various reasons, or can be directly evaluated with the use of the method. For example, an organ in a diagnostic image data set can be localized in order to subsequently determine parameters (for example its volume).

Consequential spatial information of the target volume are obtained with the use of the statistical model. For this purpose, a start position for a generated model instance of the model can initially be established under consideration of the type of the target volume to determine the location information, for example using an ellipsoid model of the torso of a patient, and the model instance can be adapted to the image data in the planning image data set in an optimization process, wherein the location information is obtained from the adapted model instance after termination of the optimization process.

A start position must consequently initially be located. How this can best be established depends on the type of the target volume. For example, if this is an organ arranged in the torso of a patient, its rough position in the torso is relatively well known. To automatically locate the start position, for example, the torso can simply be considered as an ellipsoid. The relative position in the ellipsoid at which the corresponding organ is typically located is then assumed. In practice, the first and second moments from the planning image data set according to which the ellipsoidal torso can be defined are determined for this purpose, wherein the start position can then be selected.

In an embodiment, the optimization process include the steps of generating a sub-model that comprises those correspondence points of the statistical model for which corresponding image points are present in the planning image data set, calculating the current profiles of the correspondence points of the sub-model using the planning image data set, calculating a most probable displacement (shift) for each correspondence point of the sub-model using the current profiles and the respective statistical profiles, calculating that transformation that best reproduces the most probable displacement projecting the transformed sub-model to the statistical sub-model, and repeating the preceding steps until the model converges.

As noted above, the planning image data set should cover as little as possible for a fast implementation of the method. The spatial coverage of the model data sets will therefore exceed that of the planning order distribution system. Fewer data points are therefore located in the planning image data set than in the statistical model of the target volume. Therefore, a sub-model must be generated in which those correspondence points of the statistical model are located for which there are correspondences in the planning image data set. The corresponding profile of the greyscale value distribution can subsequently be respectively calculated for the current, existing correspondence points, and these profiles can then be compared with the profiles of the statistical sub-model. The transformation for the most probable displacement can be calculated from these data, and the statistical sub-model can be accordingly transformed. Upon convergence of the calculations, that statistical model or sub-model has been found that best reflects the measurement data.

As already mentioned, the method according to the invention can be used to control the further acquisition operation of image data. In particular, the acquisition of a second image data set (in particular of a magnetic resonance image data set) can thereby be controlled using the location information. This is particularly advantageous when the image acquisition device used to acquire the planning image data set is used to acquire the second image data set. The planning image data set can in turn be composed of localizer exposures. The patient advantageously remains unmoved between the acquisition of the second image data set and the acquisition of the planning image data set. Defined movements (in particular of the patient table) can be incorporated into the spatial information.

Alternatively, it is also possible to acquire an overview image data set, and the planning image data set is registered with the overview image data set and a second image data set is acquired with the patient unmoved in comparison to the overview image data set, wherein the control of the acquisition ensues using the registration and the spatial information. For example, such a scenario can occur when a diagnostic data set acquired in a past examination or even some other image data set is used. Then it is naturally also necessary to establish a correlation between the planning image data set and the coordinate system of the image acquisition device or, respectively, of the current bearing and position of the patient. This occurs with the aid of the overview image data set. For example, these can again be localizer exposures.

The acquisition of the second image data set can be controlled in many kinds of ways. The spatial information can thus be used to determine image acquisition parameters of slices to be acquired. This is primarily helpful in magnetic resonance acquisitions. The laborious manual marking of slices to be acquired is consequently discarded in a display of the planning image data set. Alternatively or additionally, the spatial information can be used for positioning of a navigator. With the use of the known position, orientation and shape of the target volume, by means of suitable algorithms it is easily possible to enable an idea positioning of a navigator (for example PACE) that is far less error-prone.

Furthermore, the spatial information can be used for positioning of the patient. For example, an ideal positioning of a patient bed in a magnetic resonance apparatus can be determined so that maximum homogeneity predominates in the target volume.

As a last example, it is ultimately advantageous to use the spatial information to adapt a measurement protocol in magnetic resonance acquisitions. For example, the repetition time can be optimized in what are known as link acquisitions.

Often it is also possible that a larger number of image data sets are acquired in the framework of a complete examination or an examination in multiple steps. For steady improvement and optimization of the spatial information, it can be useful to use the second image data set as a planning data set for a further implementation of the method. The establishment of the location information is therefore continuously improved iteratively from acquisition to acquisition. The results of the last adaptation of the statistical model can always be used as start values.

Since the same adapted model instance ultimately results with different exposures (thus in different image data sets) given the adaptation of the model to the corresponding patients, thus these ultimately differ only due to the positioning of the patient during the acquisition (thus in bearing and positioning and possibly due to deformation), the two mentioned image data sets can nevertheless be connected via comparison of marked points of these two model instances. Thus, first and second location information can be obtained from a first planning image data set acquired in a first examination and a second planning image data set serving for planning a follow-up examination, with both the first location information and the second location information being used for control. For example, in the first planning image data set a specific point can be located at which (for example) an irregularity exists that should be examined in more detail the scope of a follow-up examination. Since the model instances significantly correspond, the same point of interest can naturally also be located in the instance of the statistical model that is adapted to the second planning image data set. The items of information obtained from two planning image data sets are thus advantageously correlated with one another in order to localize the actual region of interest for the follow-up examination in the second planning image data set and to control the follow-up examination operation accordingly. In summary, given different position, orientation and/or shape of the target volume during the acquisition of the first planning image data set and during the acquisition of an additional image data set that is to be controlled, the first and the second items of spatial information serve to determine a spatial relationship (in particular a registration) based on which the control ensues. A simple registration is also consequently possible using the method.

In another variant of the method, evaluation information about the target volume can be determined under consideration of the spatial information in the framework of a control of the evaluation operation. For example, a start value for a segmentation process can be determined from the location information. Where the adaptation of the statistical model alone already represents a very good segmentation, as a start value for a finer segmentation algorithm it can be a starting point for even more precise and better results.

Alternatively or additionally, the spatial information is drawn upon to determine physiological parameters or data. For example, such parameters or data can be the volume of an organ or the number of lesions occurring therein or the volume proportion of the lesions in the organ. The perfusion of the target volume can also be determined. The spatial information is thereby primarily used to limit the region used to obtain the parameters or data. For example, from the image data set only the portion that also belongs to the target volume is considered, and then the physiological parameters or data are determined from this sub-image data set.

However, the method is also applicable when multiple target volumes are visible in a planning image data set. Spatial information of all target volumes can then be determined using a respective statistical model per target volume. In a subsequent step, for example, an image acquisition device can be controlled so that, for each of these target volumes, second image data set that show only these target volumes are generated. The method also turns out to be particularly advantageous given the association of conspicuities with specific target volumes or organs. The spatial information can be used to associate determined physiological parameters or data with target volumes. For example, the number of lesions can therefore be displayed for all organs of the lower abdomen. For this such lesions are initially determined in an entire planning image data set, including their position. If the position then lies within a target volume localized with the aid of the statistical model, thus within a specific organ, it is associated with this organ. This is naturally possible not only for lesions but also for other abnormalities (for example carcinomas) that are then associated with different target volumes.

BRIEF DESCRIPTION OF THE DRAWINGS

FIG. 10 schematically illustrates the calculation of the most probable displacement.

DESCRIPTION OF THE PREFERRED EMBODIMENTS

Figure 3:
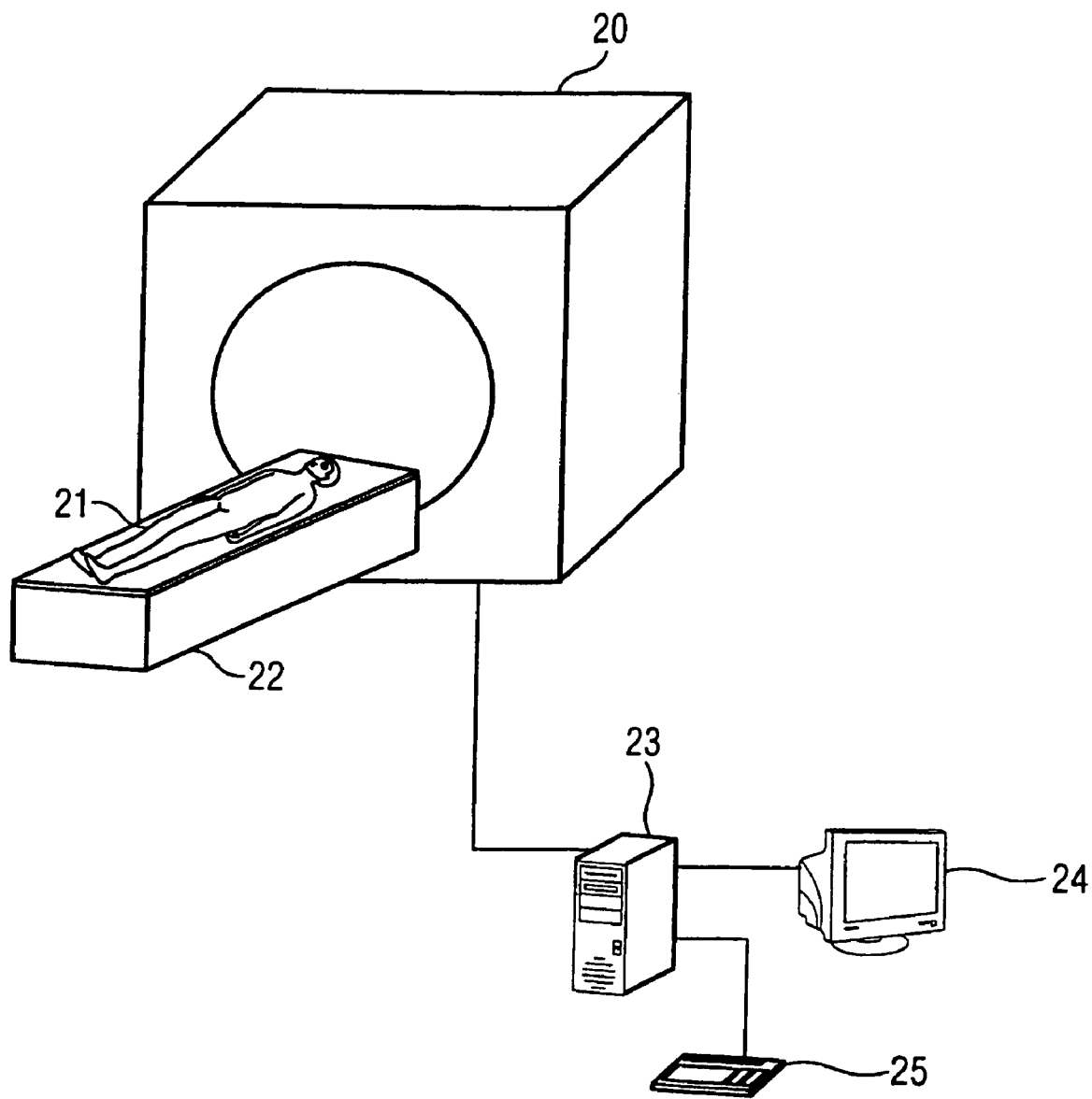
FIG. 3 schematically illustrates a magnetic resonance system for implementation of the method according to the invention.
Figure 4:
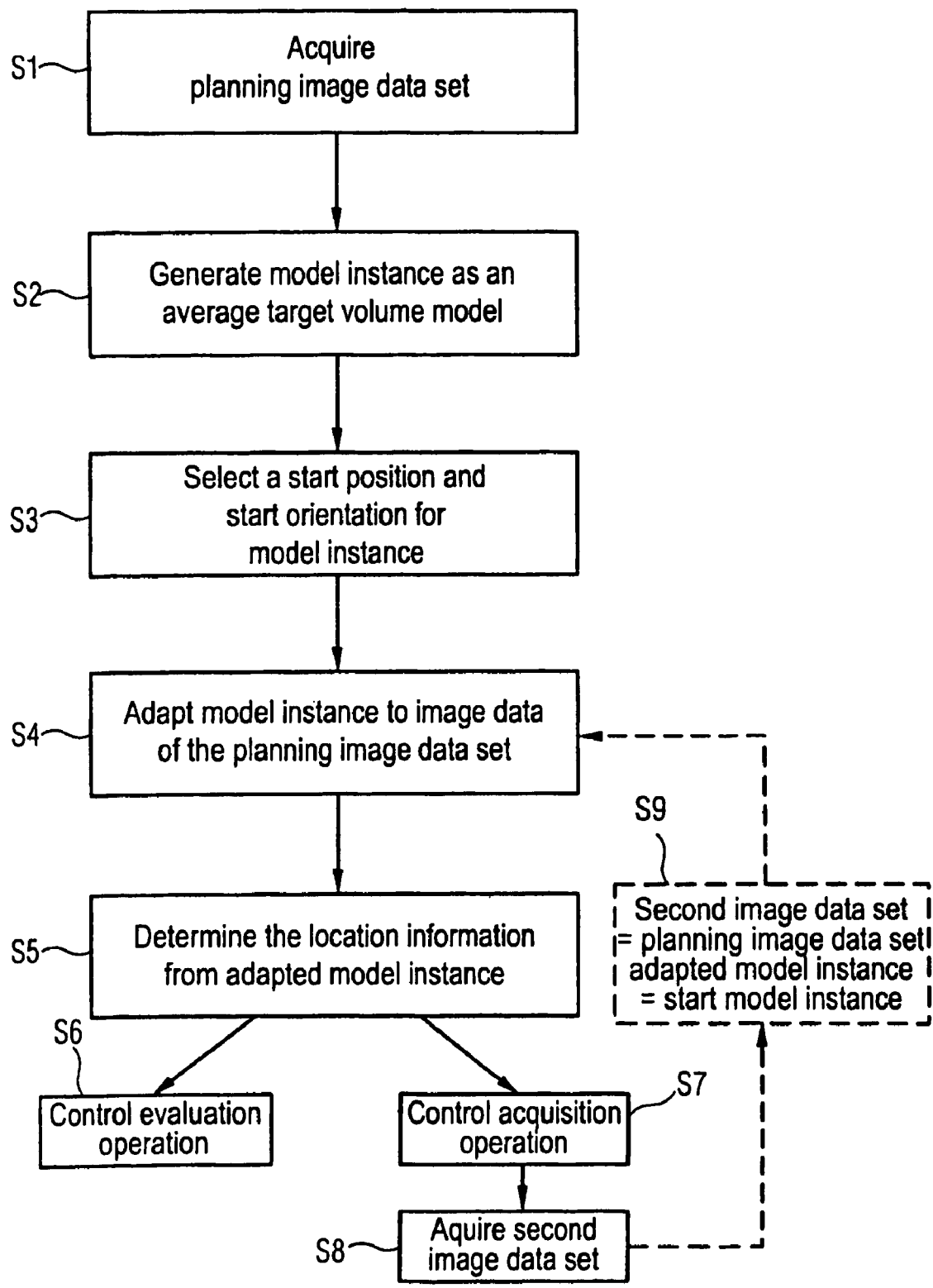
FIG. 4 is a flow chart of an embodiment of the method according to the invention.

FIG. 3 shows a magnetic resonance system 20 as an example for implementation of the method according to the invention. It is also possible to implement the method with radiation-based imaging modalities and even other imaging modalities, wherein the goal of the method would be less in time savings than in a reduction of the radiation exposure.

To create the statistical model, various patients 21 are moved into the magnetic resonance system 20 on a patient bed 22. Respective image data sets (what are known as model data sets) are acquired to create the statistical model. Additional measurements as the acquisition of high-resolution model data sets are not provided with these patients 21. The model data sets are then relayed to a computer 23 equipped with monitor 24 and keyboard 25. Whether the same patient or different patients are respectively used for different target volumes (for example brain, liver, kidneys or also the aorta and the carotids) is incidental. It is only important that sufficient model data sets in order to be able to draw statistical conclusions are respectively available for modeling for a specific target volume. The statistical spread in the model data sets can thereby be reduced when sub-groups whose variance among one another is low can be located in the patients. For example, a division into children and adults or children, women and men, or generally in an age division (which can occur according to decades, for example) is possible. Depending on the subject to be examined, the most fitting statistical model can then be selected to implement the method according to the invention.

There are two strategies to get from the model data sets to the statistical models.

Figure 1:
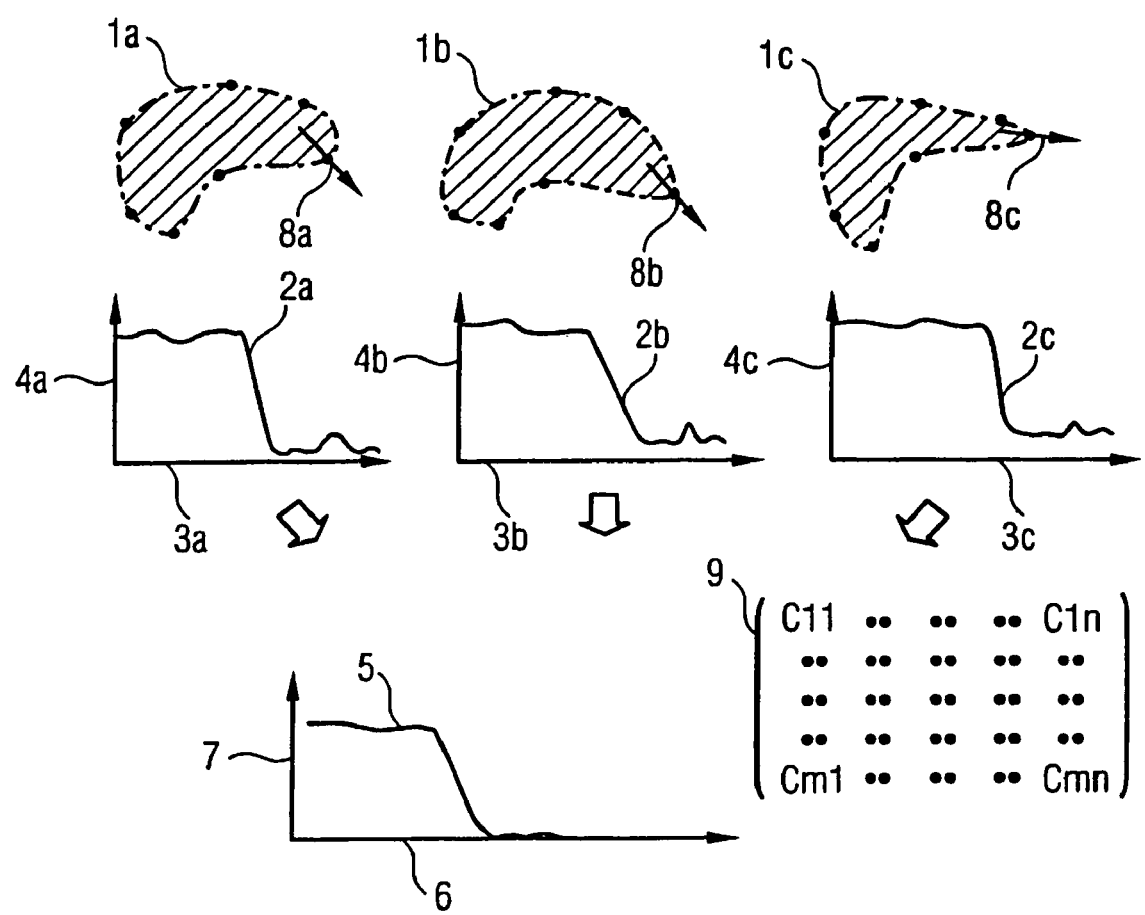
FIG. 1 schematically illustrates production of a statistical model by means of the "offline strategy".

FIG. 1 shows the "offline strategy". Correspondence points are thereby established on the surfaces of the target volumes of the model data sets. The profiles of the greyscale values are then determined in the direction of the surface normals for every correspondence point. One part of the data points of the profiles thereby lies within the target volume, one part outside the target volume and one part in the transition region. An exact separation of the target volume from the environment (characterized by a jump in the profile) is not possible in reality.

The curves 2a, 2b and 2c therefore also show not a jump but a steady transition. The curves 2a, 2b and 2c thereby show the profile of the grey values that are indicated by the surface normals 8a, 8b and 8c of the target volumes 1a, 1b and 1c. The x-axes 3a, 3b and 3c respectively point in the direction of the surface normals 8a, 8b and 8c while the y-axes 4a, 4b and 4c indicate relative intensity profiles. A greyscale value profile is thus initially obtained for each model data set and every correspondence point. In the "offline strategy", the statistical model is now formed in that an average value is formed from the greyscale value profiles of corresponding correspondence points, and a corresponding covariance matrix is calculated for this. The averaging thus respectively ensues across the model data sets, and as many greyscale value profiles and covariance matrixes are obtained as correspondence points that have been established.

Figure 2:
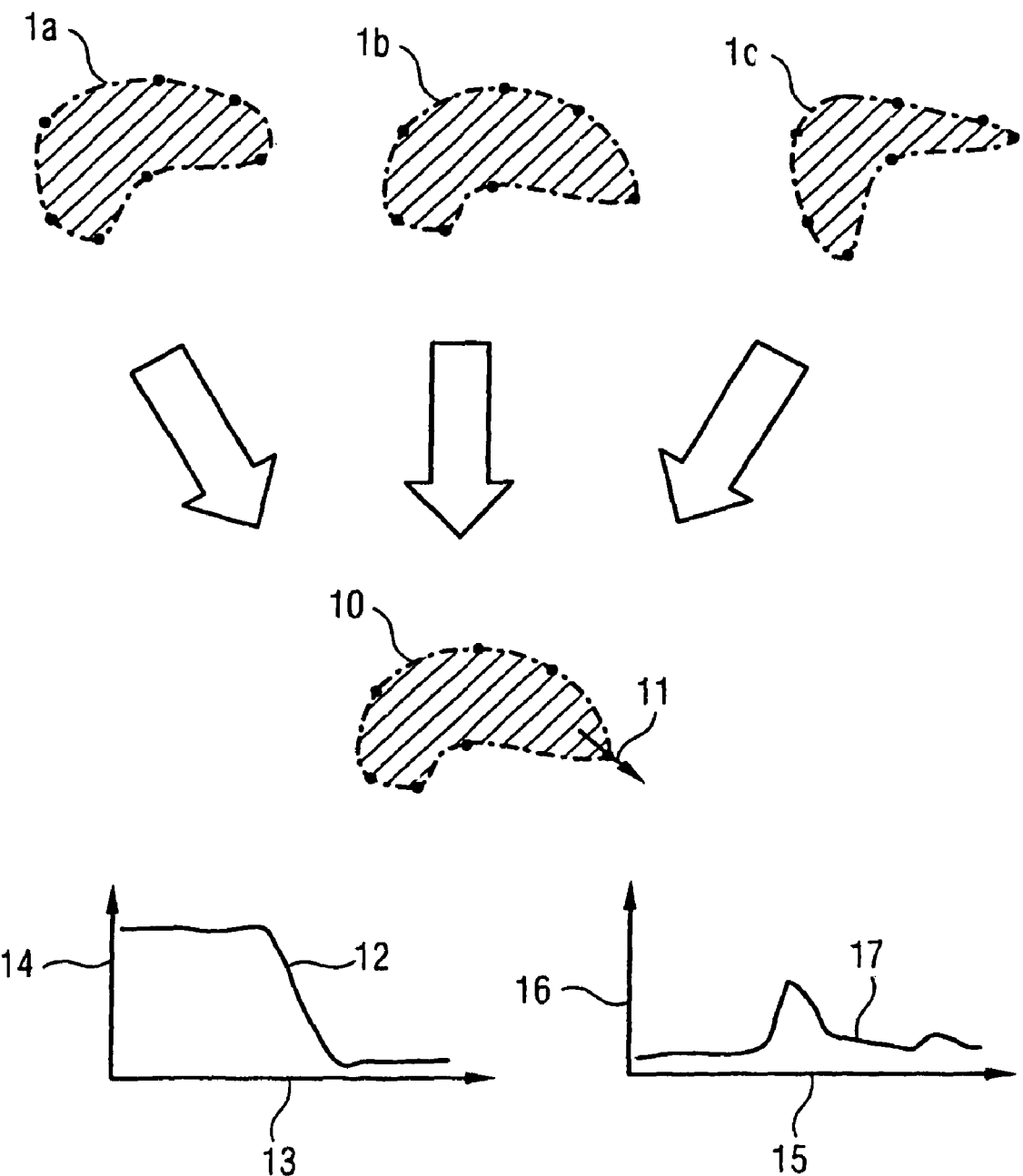
FIG. 2 schematically illustrates production of a statistical model by means of the "on-the-fly strategy".

The procedure in the "on-the-fly strategy" is something different, as is visible in FIG. 2. Here the target volumes 1a, 1b and 1cc are also provided with correspondence points; however, a reference image is then acquired from these via transformation. A normalized average image and a normalized variance image can then be calculated. Not only are greyscale value profiles obtained with regard to the surface normals, but also in all arbitrary directions for every correspondence point. In the normalized average image 10, the surface normal 11 is drawn for illustration. Analogous considerations can be implemented at this point for every profile orientation. The corresponding greyscale value profile 12 is plotted over the x-axis 13, which lies in the direction of the surface normal 11. The y-axis 14 indicates the intensity distribution of the greyscale profile of the average image 10 at the point of the surface normal 11. Corresponding specifications can also be presented for the variance. The x-axis 15 corresponds to the x-axis 13 but the variance is plotted on the y-axis 16; the corresponding curve 17 is likewise mapped in FIG. 2.

Figure 5:
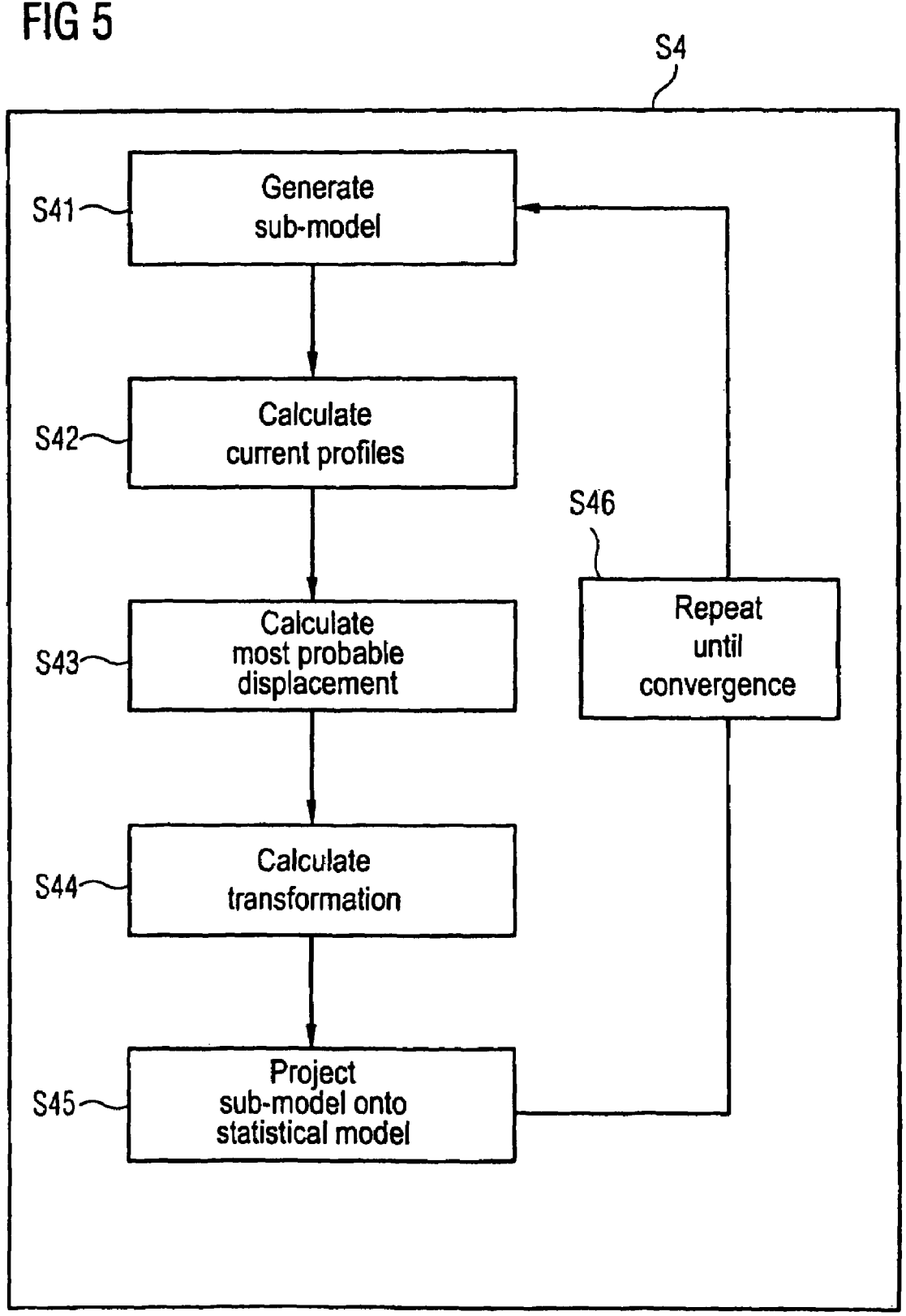
FIG. 5 is a flow chart of Step S4.
Figure 6:
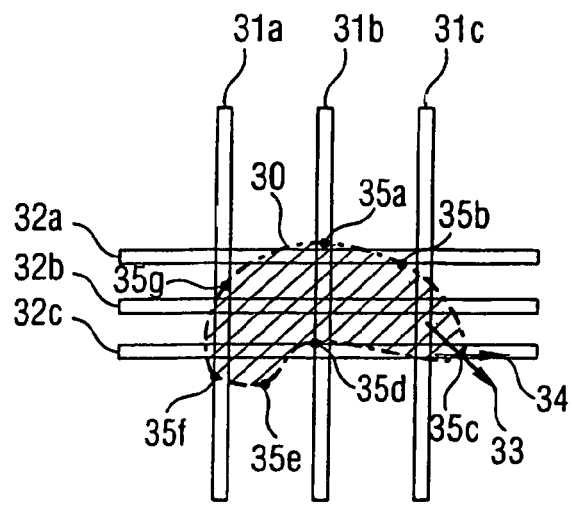
FIG. 6-9 schematically illustrates the model adaptation.

FIG. 5 shows how the average model is adapted to the values of the planning image data set. In a first step S4, a sub-model is generated. The statistical model was acquired with high resolution or, respectively, with full coverage in order to obtain optimally location information and size information of the target volume. By contrast, the planning image data set is for the most part acquired with a low resolution or coverage in order to save time. Therefore not every correspondence point in the statistical model has a correspondence in the planning image data set. Therefore, those correspondence points of the statistical model that have a correspondence in the planning image data set are selected in the sub-model. In addition to the specification of the correspondence points, the statistical model also contains a greyscale value profile for every correspondence point; corresponding greyscale value profiles then likewise exist in the sub-model for every correspondence point. In addition to these previously known and previously calculated greyscale value profiles, the current profiles are calculated in Step S42; these are the profiles that can be obtained from the planning image data set. Following this, the most probable displacement is calculated for every correspondence point, via which the profile known from the statistical model can be transformed into the current profile. In Steps S42 and S43 it should be noted that, given the presence of a statistical model based on the "offline strategy", only profiles with regard to a surface normal can be used, while profiles in arbitrary directions can be used given use of a statistical model based on the "on-the-fly strategy". An additional difference for the two different strategies also arises in the calculation of the probable displacement. For example, in the "offline strategy" it ensues via the Mahalanobis distance of the profile while in the "on-the-fly strategy" the minimal Gaussian distance is used, for example. The definition of the Mahalanobis distance is:

$$d_{Mahalanobis} = (p-\bar{p})^{1} * C^{-1}(p-\bar{p}).$$

wherein p thereby stands for the profile and C for the covariance. The Gaussian distance is defined by:

$$d_{Gauss} = \sum_i \frac{(p_i - \bar{p}_i)^2}{\sigma_i^2},$$

wherein the $p_i$ are the individual values of the profile and the $\sigma_i$ are the variances of the points. A transformation of the sub-model that best reproduces the most probable displacements is subsequently calculated in Step S44. The sub-model transformed in such a manner is then projected onto the statistical sub-model in Step S45 according to the formula $$b = P_{sub}^{-1} * (x_{sub} - \underline{x_{sub}}).$$

The values of b are thereby to be limited to a valid range. Steps S41-S45 are then repeated until the model converges. The statistical average model was thus varied until the data of the planning image data set are reproduced with the greatest probability. FIG. 6-9 show a graphical representation of the adaptation of the statistical model to the planning image data set. The planning image data set thereby consists of six localizer images, wherein three parallel slices 31a, 31b and 31c were respectively acquired as well as slices 32a, 32b and 32c perpendicular to the slices 31a, 31b and 31c and in turn parallel to one another. The statistical average model 30 with the correspondence points 35a-35g is then placed in these data. As can be seen, correspondences are found in the planning image data set for the correspondence points 35a, 35b, 35c, 35d, 35f and 35g, however not for the correspondence point 35e. This is therefore absent in the sub-model. The surface normal 33 is drawn as an example for the correspondence point 35c, as well as a freely oriented vector 34. These represent the greyscale value profiles to be obtained. Here the advantage of the "on-the-fly strategy" is clear. While only the data points that are indicated by the surface normal 33 are available in the "offline strategy", the points indicated by the vector 34 are also available in the "on-the-fly strategy"; significantly more data are thus available for calculation of the displacement of the greyscale value profiles.

Figure 8:
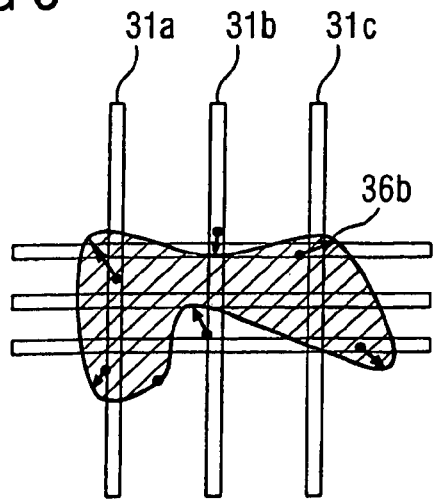
Figure 9:
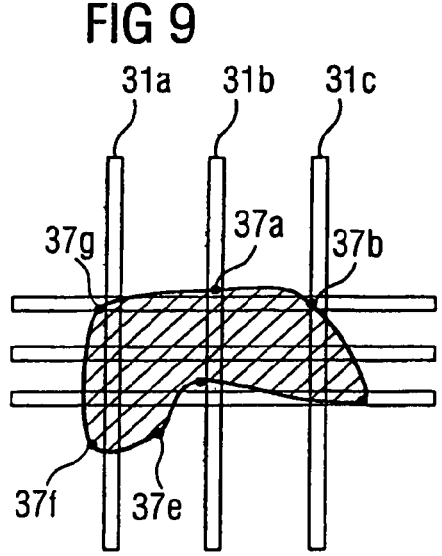

The most probable displacements 36a, 36b, 36c, 36d, 36f and 36g for the respective correspondence points are respectively plotted for the correspondence points of the sub-model. After implementing this displacement, a new sub-model 38 results (as shown in FIG. 8). The correspondence points displaced in such a manner are then transformed to the most probable model instance 39 by a similarity transformation and projection onto the sub-model, as FIG. 9 shows. A high resolution statistical model 39 of the target subject could thus be created by means of 6 quick localizers of the planning image data set, wherein both the measurement of the planning image data set and the calculation of the most probable model instances could take place quickly.

Figure 7:
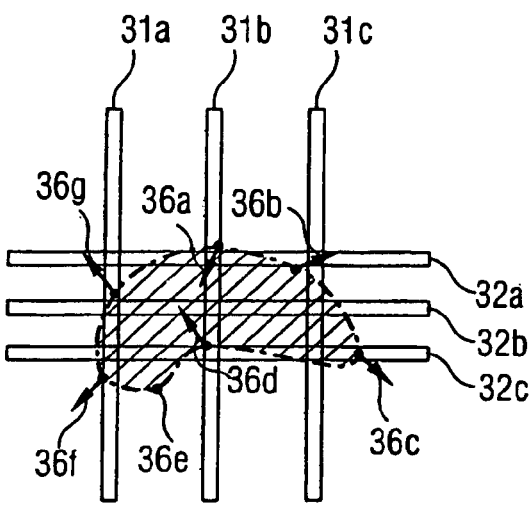

FIG. 7 schematically shows the discovery of the most probable displacement. Three possible displacements 42a, 42b, 42c are conceivable for the correspondence point 41 of the sub-model 40. The current profile 44 is taken from the planning image data set while the possible profiles 43a, 43b and 43c based on the displacement are taken from the statistical model. As can be recognized, a maximum correlation results for the displacement 42b, which therefore is selected for the correspondence point 41. The method proceeds accordingly for all further correspondence points of the sub-model 40.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a device to implement acquisition and/or evaluation of image data in a medical examination, comprising the steps of:
   supplying a previously acquired planning image data set, entirely or partially covering a target volume, to a processor;
   in said processor, accessing a statistical model based on anatomy of at least one subject and comprising at least one greyscale value distribution in a region of a surface of the target volume;
   in said processor, automatically determining spatial information of the target volume using said statistical model;
   establishing correspondence points on said surface of said target volume that correspond to points in said statistical model and determining, in said processor, grayscale values in the respective directions of surface normals for each of said correspondence points of said target volume, as profiles and normalizing said profiles and determining an average profile representing the statistical model and a covariance matrix representing statistical deviations for each correspondence point from said respective profiles; and
   from said processor, generating an output signal representing said spatial information and using said output signal to control said device for said acquisition and/or evaluation of image data.

2. A method as claimed in claim 1 comprising generating said statistical model based on a plurality of examination subjects.

3. A method as claimed in claim 1 comprising automatically determining a reference image in said processor from said correspondence points, by transformation of all model data sets to said average model.

4. A method as claimed in claim 3 comprising automatically determining, in said processor, a normalized average image representing an additional statistical model and a normalized variance image representing statistical deviations, from a reference image.

5. A method as claimed in claim 1 comprising generating a planning image data set using localizer exposures.

6. A method as claimed in claim 1 comprising generating a planning image data set using previous diagnostic image data from a subject.

7. A method as claimed in claim 1 wherein said planning image data set is a first image data set, and acquiring a second image data set with said device by controlling said device according to said spatial information.

8. A method as claimed in claim 7 comprising using said device to also acquire said planning image data set.

9. A method as claimed in claim 7 comprising providing said processor with an overview image data set and registering said planning image data set in said processor with said overview image data set, and acquiring said second image data set with the subject in a same position as for the overview image data set, and controlling acquisition of said second image data set using the registration and the spatial information.

10. A method as claimed in claim 7 comprising using the spatial information to determine image acquisition parameters of slices in said second image data set.

11. A method as claimed in claim 7 comprising using the spatial information for positioning a navigator for acquiring said second image data set.

12. A method as claimed in claim 7 comprising using the spatial information to position the patient for acquiring said second image data set.

13. A method as claimed in claim 7 comprising using the spatial information to adapt a measurement protocol of a magnetic resonance acquisition by said device, for acquiring said second image data set.

14. A method as claimed in claim 7 comprising using said second image data set as a planning data set for a further implementation of said method.

15. A method as claimed in claim 7 wherein said spatial information is first spatial information, and acquiring second spatial information from said second image data set, and using both said first and second spatial information for controlling said device to implement a follow-up examination of said subject.

16. A method as claimed in claim 15 comprising, from said first and second spatial information, identifying a spatial relationship between the subject in the acquisition of the first image data set and the acquisition of the second image data set, and controlling said follow-up examination using said relationship.

17. A method as claimed in claim 1 comprising evaluating information characterizing said target volume in real time during generation of said spatial information in an evaluation procedure.

18. A method as claimed in claim 17 comprising, from said spatial information, generating a start value for a segmentation procedure in an evaluation procedure.

19. A method as claimed in claim 17 comprising utilizing said spatial information to determine physiological parameters or data in an evaluation procedure.

20. A method as claimed in claim 1 comprising utilizing spatial information from multiple target volumes in said planning image data set, and for each of said multiple target volumes, accessing a respective statistical model comprising a grayscale distribution for the surface of the respective target volume.

21. A method as claimed in claim 20 comprising associating the respective spatial information from the multiple target volumes to determine physiological parameters or data in an evaluation procedure.

22. A method for controlling a device to implement acquisition and/or evaluation of image data in a medical examination, comprising the steps of:
- supplying a previously acquired planning image data set, entirely or partially covering a target volume, to a processor;
- in said processor, accessing a statistical model based on anatomy of at least one subject and comprising at least one greyscale value distribution in a region of a surface of the target volume;
- in said processor, automatically determining spatial information of the target volume using said statistical model initially establishing a start position of the subject for generating said statistical model dependent on a characteristic of said target volume, and adapting the statistical model to a planning image data set in an optimization procedure in said processor, thereby obtaining adapted spatial information after said optimization process;
- in said optimization process in said processor:
  generating a sub-model comprising correspondence points of the statistical model for which corresponding image points in a planning image data set exist, calculating profiles of the correspondence points of the sub-model using the planning image data set, calculating a most probable displacement for each correspondence point of the sub-model using the current profiles and the respective statistical profiles, calculating a transformation that best reproduces a most probable displacement, transforming the sub-model using said transformation, to obtain a transformed sub-model, and projecting said transformed sub-model onto the statistical sub-model, and repeating the steps of generating a sub-model, calculating current profiles, calculating a most probable displacement, calculating a transformation, and projecting the transformed sub-model, until convergence of said transformed sub-model; and
- from said processor, generating an output signal representing said adapted spatial information and using said output signal to control said device for said acquisition and/or evaluation of image data.

23. A method as claimed in claim 22 comprising utilizing an ellipsoid model of the torso of the subject as said start position.

* * * * *